(12) United States Patent
Buckner (10) Patent No.: US 6,312,608 B1
(45) Date of Patent: *Nov. 6, 2001

(54) STERILIZING CONDUIT FOR BEVERAGE STORAGE AND DISPENSING

(76) Inventor: Lynn Buckner, P.O. Box 609, Chickamauga, GA (US) 30707

( * ) Notice: Subject to any disclaimer, the term of this patent is extended or adjusted under 35 U.S.C. 154(b) by 0 days.

This patent is subject to a terminal disclaimer.

(21) Appl. No.: 09/533,823

(22) Filed: Mar. 24, 2000

Related U.S. Application Data (63) Continuation-in-part of application No. 09/129,782, filed on Aug. 6, 1998, now Pat. No. 6,090,281.

(51) Int. Cl.[7] .................................. A61L 2/00; B01D 1/68
(52) U.S. Cl. ..................... 210/748; 210/760; 210/764; 239/12
(58) Field of Search .............................. 210/85, 175, 205, 210/103, 138, 149, 741, 748, 749, 742, 760, 764, 636, 199; 222/386.5, 92; 138/20; 422/24, 28, 186.3; 220/495.01, 495.03; 239/12, 17

(56) References Cited

U.S. PATENT DOCUMENTS

| | | | |
|---|---|---|---|
| 3,122,000 | * 2/1964 | Sirocky | 222/386.5 |
| 3,679,055 | * 7/1972 | Clark et al. | 210/321 |
| 3,802,464 | * 4/1974 | Frank et al. | 138/30 |
| 4,274,970 | * 6/1981 | Beitzel | 210/748 |
| 4,836,409 | * 6/1989 | Lane | 138/30 |
| 5,068,030 | * 11/1991 | Chen | 210/149 |
| 5,124,050 | * 6/1992 | Ushimaru et al. | 210/748 |
| 5,358,635 | * 10/1994 | Frank et al. | 210/257.2 |
| 5,389,254 | * 2/1995 | Sherman | 210/138 |
| 5,531,908 | * 7/1996 | Matsumoto et al. | 210/764 |
| 5,660,720 | * 8/1997 | Walling | 210/85 |
| 5,686,893 | * 11/1997 | Jeon | 210/103 |
| 5,766,453 | * 6/1998 | Morellato et al. | 210/175 |

* cited by examiner

Primary Examiner—David A. Simmons
Assistant Examiner—Frank M. Lawrence (57) ABSTRACT

A method for containing and dispensing a sterile liquid includes the steps of providing a variable volume liquid container, the container having the capacity to be filled with, and dispense a liquid while isolating the liquid from any gaseous substance, the variable volume liquid container having a sterilizer disposed within the liquid when the liquid is stored in the container. The filling and dispensing conduit having sterilizing properties. The variable volume liquid container can also include an apparatus immersed in the liquid to heat or cool the liquid to a predetermined temperature.

17 Claims, 15 Drawing Sheets

STERILIZING CONDUIT FOR BEVERAGE STORAGE AND DISPENSING

This application is a continuation-in-part of U.S. patent application Ser. No. 09/129,782, filed Aug. 6, 1998 now U.S. Pat. No. 6,090,281.

FIELD OF THE INVENTION

The present invention relates to the field of drinking water containers and dispensers. More particularly, the present invention relates to the field of storage containers and dispensers that can purify or sterilize water and maintain the water in a pure or sterile state, while filling or dispensing through a conduit having sterilizing abilities, or over a water fall having the capacity to maintain sterilization

BACKGROUND OF THE INVENTION

Liquids are commonly stored for extended periods of time in storage containers, and dispensed at a later time. An example is a thermos cooler or five gallon bottled water container which can hold gallons of potable liquid, and thereby transport the liquid to a place where the liquid can be utilized as desired.

Perhaps the biggest problem associated with storing liquid that requires periodic, dispersing while being stored is contamination of the liquid. Large amounts of liquid will be ruined and unusable if they are contaminated by germs, bacteria, etc. before being consumed particularly when the stored liquid is exposed to the atmosphere during periodic dispensing. Dispensing techniques have the capacity to contaminate liquids which were stored in a sterile state.

Another problem associated with storing liquid over a long period of time is that even if the liquid is stored in an insulated environment, the liquid is subject to slight temperature adjustment toward the temperature of the surroundings of the container. Lukewarm beverages are not very desirable in general, and tend to be contaminated much faster than when they are very hot or very cold.

It is therefore an object of the present invention to provide a beverage storage and dispensing container that is capable of being filled or emptied without placing the liquid in direct contact with the atmosphere or other gaseous substances.

It is another object of the present invention to provide such a container/dispenser that is able to sterilize the liquid during storage.

It is another object of the present invention to provide such a container that is able to be filled or emptied through a conduit having sterilizing capability, or flow the liquid over a water fall having sterilizing capabilities.

It is another object of the present invention to provide such a container/dispenser that is able to maintain in a temperature of a liquid over as long of a period of time as is desired.

It is a further object of the invention to provide such container/dispenser that provides these benefits for a much liquid as is conceivably transportable, while at the same time, making small amounts of the store liquid available to individuals in small portions.

It is yet another object of the invention to provide such a container/dispenser that provides all of the above benefits with easy access to further necessary power-supplied appliances and all utensils and apparatuses needed for serving and catering.

It is another object of the present invention to provide the ability for filling of the container/dispenser from a powered mobile bulk delivery system.

SUMMARY OF THE INVENTION

It is an object of the present invention to meet the above-described needs and others. Specifically, it is an object of the present invention to provide a liquid storage and dispensing container, which includes a flexible diaphragm, bladder, flexible bag bellows or other variable volume apparatus, a liquid dispenser, and a liquid sterilizer that maintains the liquid in a sterile state in the container. The liquid in the container may be any liquid such as drinking water or beverage. The sterilizer can include an ultraviolet light, an ultrasonic generator, a silver particle sterilizer, an ozone generator and injection mechanism, and other suitable sterilizing apparatuses or techniques.

Filling and dispensing conduits may have the ability to sterilize the liquid while the liquid is present in the conduit. The sterilizing means may be silver impregnated conduits, fiber optic ultraviolet light, ozone, ultrasonic or other suitable sterilizing apparatuses or techniques. An antibacterial dispenser may be provided at an end of the conduit, also having a associated sterilizing means.

A temperature adjustment device, such as a thermoelectric component may be attached to or contained inside the container. To heat or cool the stored liquid, any suitable heating or cooling apparatus may be used.

The liquid may be stored under pressure by exerting external pressure to the variable volume liquid storage container/dispenser. External pressure can be achieved by mechanical means such as a spring, or, by surrounding a liquid bladder with an inflexible cover and pressurizing an area between the flexible liquid bladder and the inflexible cover. An air compressor for example can be used to pressurize this area. If the air void is equipped with a pressure sensor, pressure relief valve and an air compressor for example, then a constant pressure can be applied to the liquid bladder thus maintaining the liquid at a given storage pressure as the liquid is dispersed.

The liquid storage and dispersing container along with its sterilizing capabilities and cooling or heating capabilities may be located near an end user who disperses sterile liquid on demand. The storage/dispensing system can be refilled by a powered mobile delivery system or other suitable liquid supply system.

The liquid storage and dispersing container along with its sterilizing capabilities can be sized for use by an end user, as a means of providing powered mobile bulk delivery in a bulk delivery system. Also, the liquid storage and dispersing container along with its sterilizing capabilities can be sized for centralized bulk storage to service mobile bulk delivery systems.

A device may be added to the container, which automatically begins and ends operation of the sterilizer. Such a device may include a timer, which provides automation of any sterilizer, such as an ultraviolet light. Another device may be added, which automatically begins and ends operation of a thermoelectric device. Such a device may include a temperature sensor. The thermoelectric device may provide heat to the liquid when a switching circuit connected to the thermoelectric device is positioned in a first state, and the device may also cool the liquid when the switching circuit is positioned in a second state.

An alarm system can include both a detector and a warning device, and activates the warning device upon an event of a container malfunction and/or upon an event of a container defect may be added to the container.

Computer hardware and software may be used to monitor and operate the sensors.

The liquid storage and dispensing container may also include an insulation layer for reducing thermal transfer between the liquid and the surroundings of the container. The container may also have a protective outer cover that surrounds the container. The method may also include the steps of pressurizing the liquid in the container, and measuring an amount of the liquid in the container. Other steps in the method may include providing work surfaces, shelves, an ice maker, and storage areas in the surroundings of the container.

Additional objects, advantages and novel features of the invention will be set forth in the description which follows or may be learned by those skilled in the art through reading these materials or practicing the invention. The objects and advantages of the invention may be achieved through the means recited in the attached claims.

To achieve these stated and other objects, the present invention may be embodied and described as set forth in the following detailed description, in the drawings, and in the claims.

BRIEF DESCRIPTION OF THE DRAWINGS

The accompanying drawings illustrate the present invention and are a part of the specification. Together with the following description, the drawings demonstrate and explain the principles of the present invention.

DETAILED DESCRIPTION OF THE PREFERRED EMBODIMENTS

Using the drawings, the preferred embodiments of the present invention will now be explained.

FIGS. 1, 2, 10, and 12 to 14 show the first embodiment of the invention in a variety of environments according to the preference of the user. The apparatus of the present invention includes a bladder 1, made of a flexible material. The bladder 1 may be made of a food grade material, and may be very elastic, formed according to the amount of liquid 4 that occupies it. An outer shell 2 actually surrounds the bladder 1 and may be formed of a rigid material that is pressure coded. An insulation layer for reducing thermal transfer between the liquid 4 and the surroundings may be placed around the outer shell 2. In a preferred embodiment of the invention, a cavity 3 is formed between the bladder 1 and the outer shell 2. The cavity 3 is filled with air or other compressible gases through a valve 6, such as a needle valve, which provides pressure as the bladder 1 is filled with liquid 4 by way of an orifice fitting 5 through a filling receptacle, thus reducing the cavity area 3. The pressure in the cavity 3 is thus exerted on the bladder 1, so that the liquid 4 in the bladder 1 is stored under pressure.

The pressure exerted in the gaseous void 3 can be maintained at a consistent pressure. As the volume changes by use of an air compressor 61 controlled by a pressure sensor 62 and a pressure relief valve 63, a pressure gauge 64 indicates the pressure in the gaseous void 3. Also in a preferred embodiment of the invention, the liquid 4 is a potable liquid such as drinking water or another beverage.

A liquid dispenser such as a discharge fitting 7 is provided as a conduit by which liquid may flow out of the container. Parts and devices that require access to the internals of the outer shell 2 or bladder 1 can have such access through one or more flanges 8. The outer shell 2 may rest on a container base 9 which stabilizes the outer shell 2 as it may become extremely heavy when large amounts of liquid 4 are stored therein.

Figure 1:
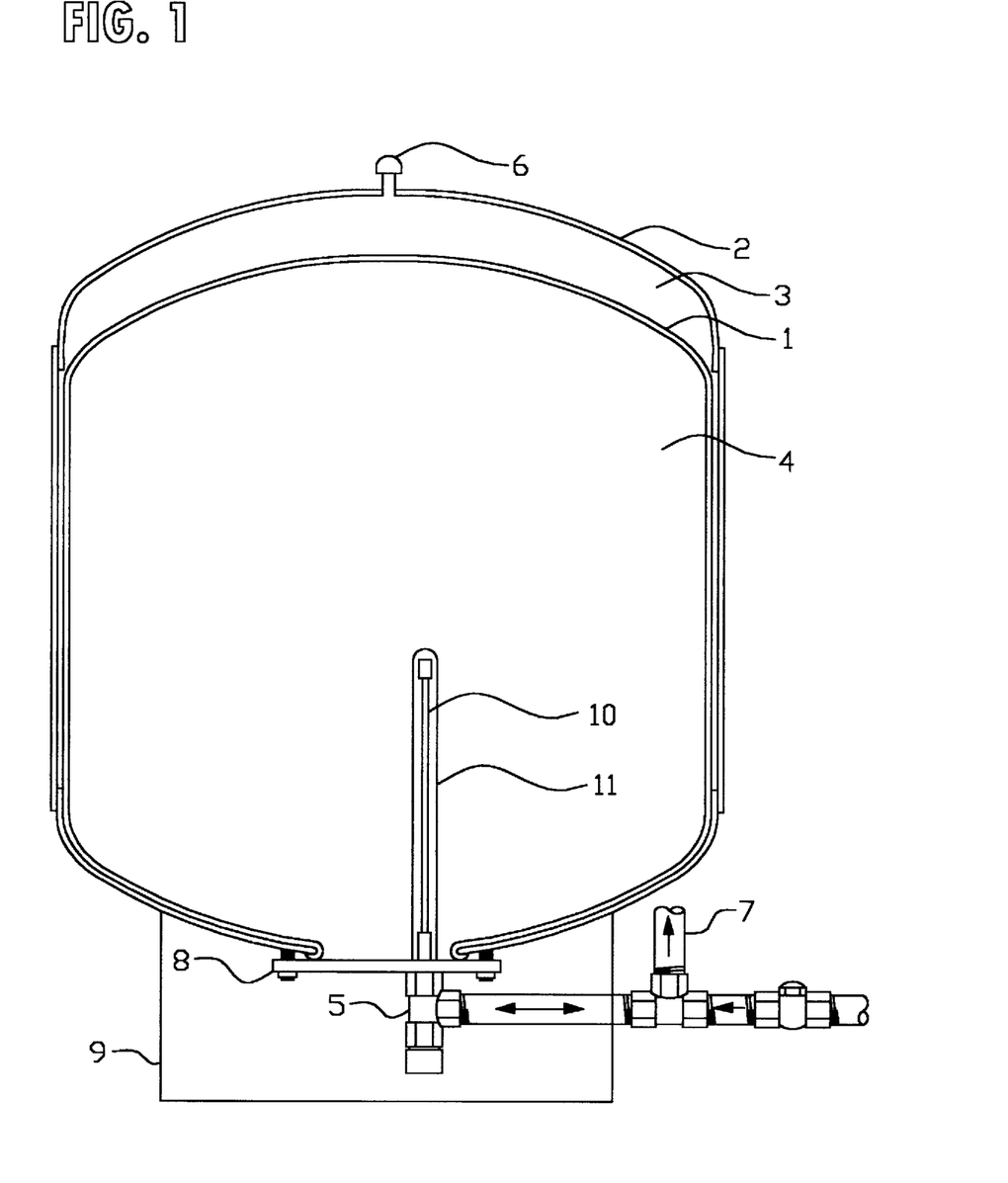
FIG. 1 shows a liquid storage and dispensing container according to a first embodiment of the invention being a bladder tank with an ultraviolet germicidal lamp disposed within it.
Figure 2:
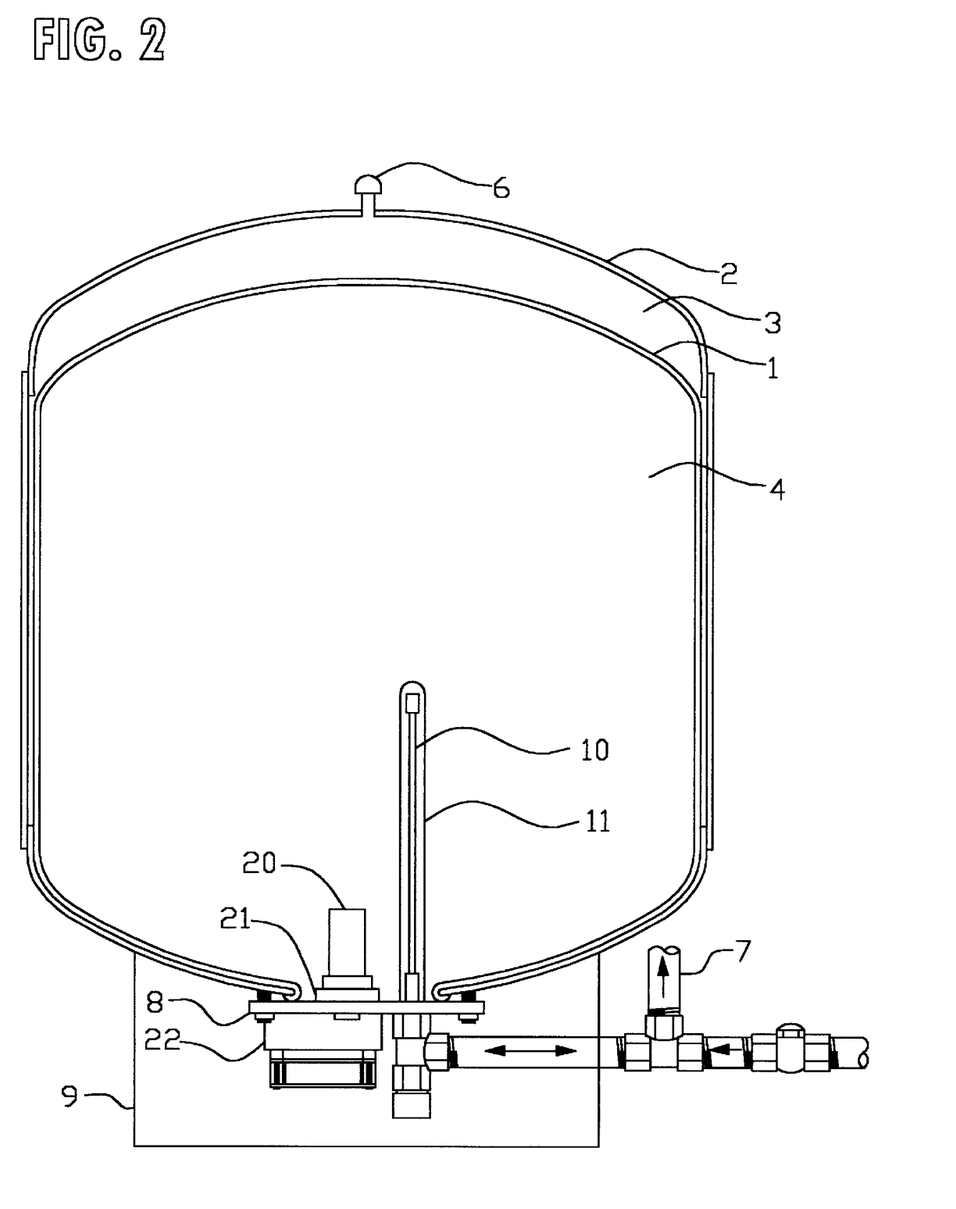
FIG. 2 shows a liquid storage and dispensing container according to the first embodiment of the invention, using both a sterilizer and a temperature adjustment unit.

A liquid sterilizer that maintains the liquid 4 in a sterile state in the container is provided in connection with the bladder 1. In a preferred embodiment-of the invention, a sterilizing light 10 is used to sterilize the liquid 4 of bacteria and germs. In a preferred embodiment of the invention, an ultraviolet germicidal lamp 10 that operates in the 180 nm wave length range is used to sterilize the liquid 4. In a more preferred embodiment, the ultraviolet lamp 10 operates in the 240 nm to 300 nm wave length range.

When an ultraviolet germicidal lamp 10 is used as a sterilizer, a quartz sleeve 11 is used to envelope the germicidal lamp 10 in order to isolate it from the liquid 4. Also, a UV transformer 12 is provided with a wiring harness, to power the ultraviolet light. A device Tl such as a timer may be connected with the UV transformer 12, which automatically begins and ends operation of the germicidal lamp 10 or any other sterilizer. Any sealing mechanism known in the art can be used to isolate the liquid 4 from the sterilizing light unit 10.

Figure 3:
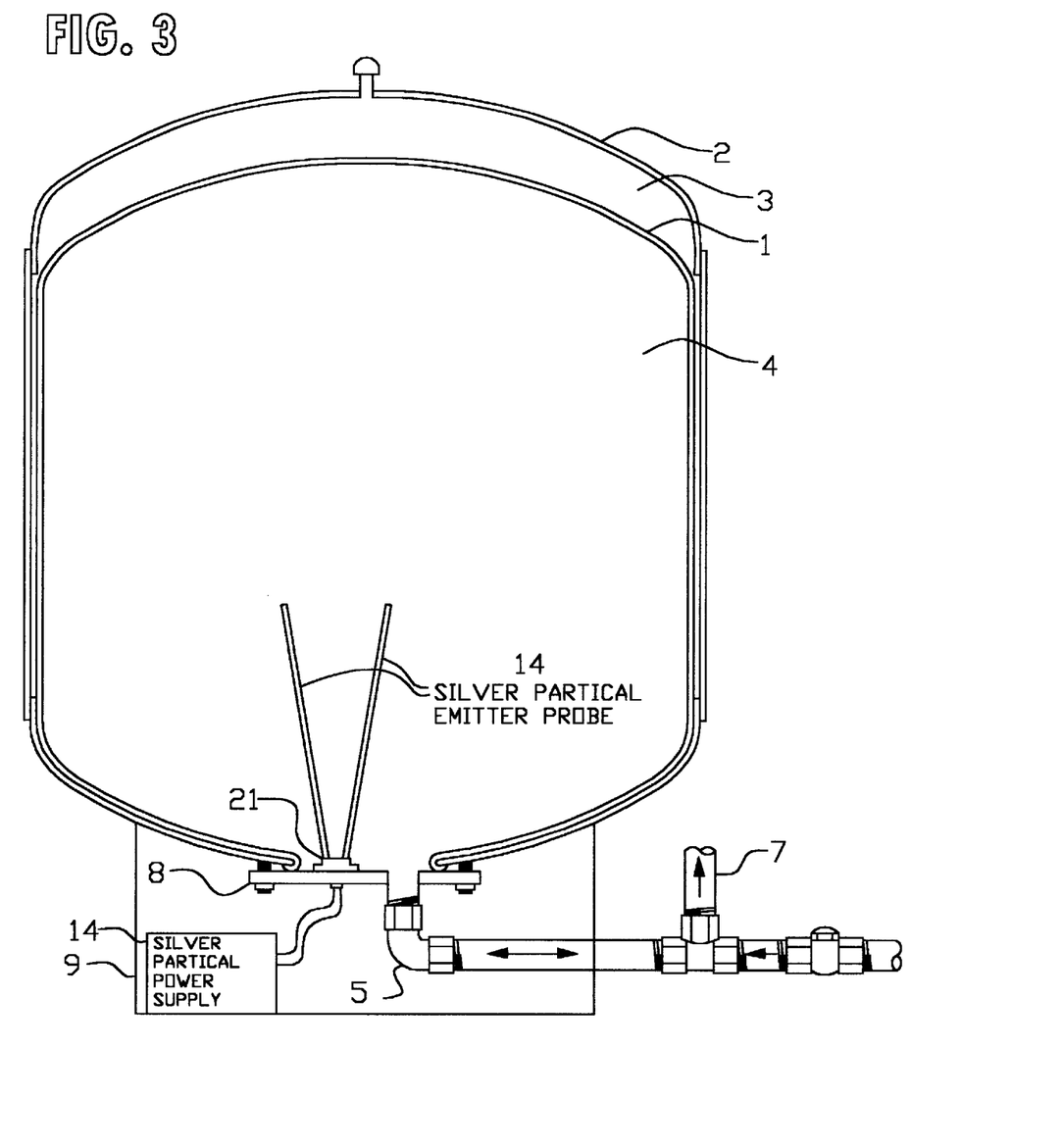
FIG. 3 shows a liquid storage and dispensing container according to a second embodiment of the invention, using a silver particle sterilizing method.

In a second embodiment of the invention shown in FIG. 3, the sterilizer is a silver particle emitter 14. According to the second embodiment, at least one silver probe is set up, using electrolysis techniques to provide silver particles which kill bacteria in the liquid 4.

Figure 4:
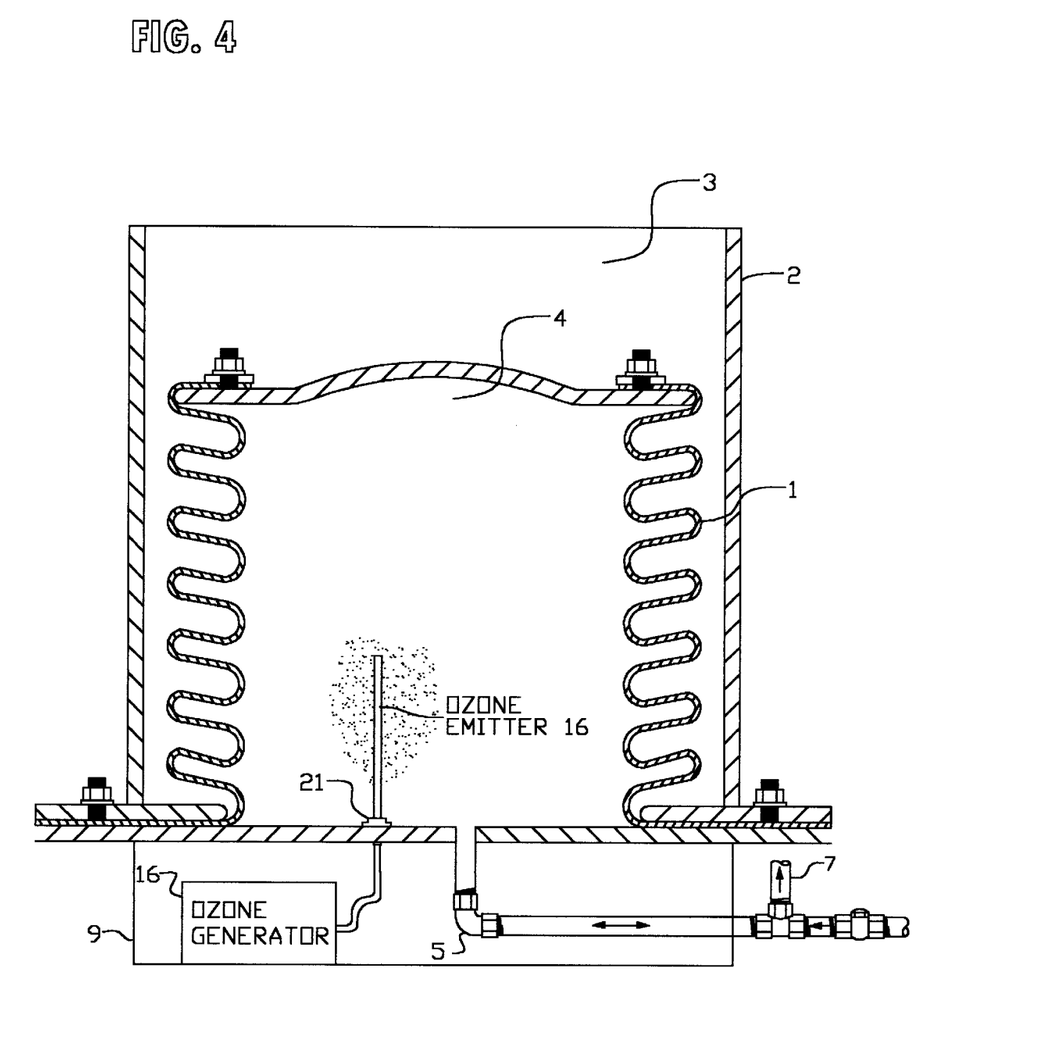
FIG. 4 shows a liquid storage and dispensing container according to a third embodiment of the invention, using an ozone emitter.

In a third embodiment of the invention shown in FIG. 4, the sterilizer is an ozone generator 16 and includes an injection mechanism which allows ozone to sufficiently contact the liquid 4 in the container.

Figure 5:
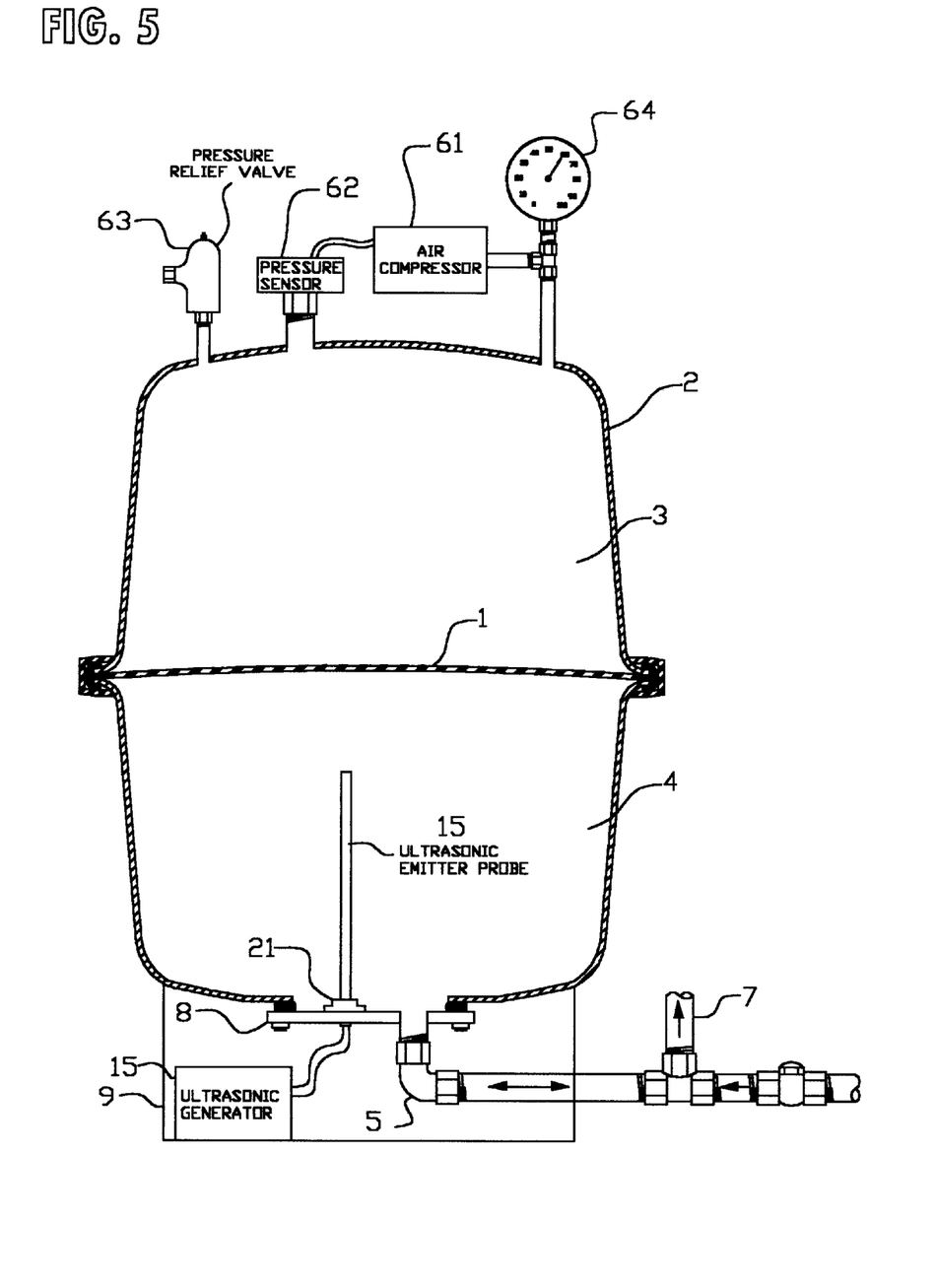
FIG. 5 shows a liquid storage and dispensing container according to a fourth embodiment of the invention, using an ultrasonic emitter. Dispensing container utilizes an air compressor, pressure sensor and pressure relief valve to maintain a given liquid pressure.

In a fourth embodiment of the invention shown in FIG. 5, the sterilizer is an ultrasonic sterilizer 15. In that embodiment, ultrasonic probes 15 are inserted into the container contacting the liquid 4, and are equipped with an ultrasonic generator.

Figure 6:
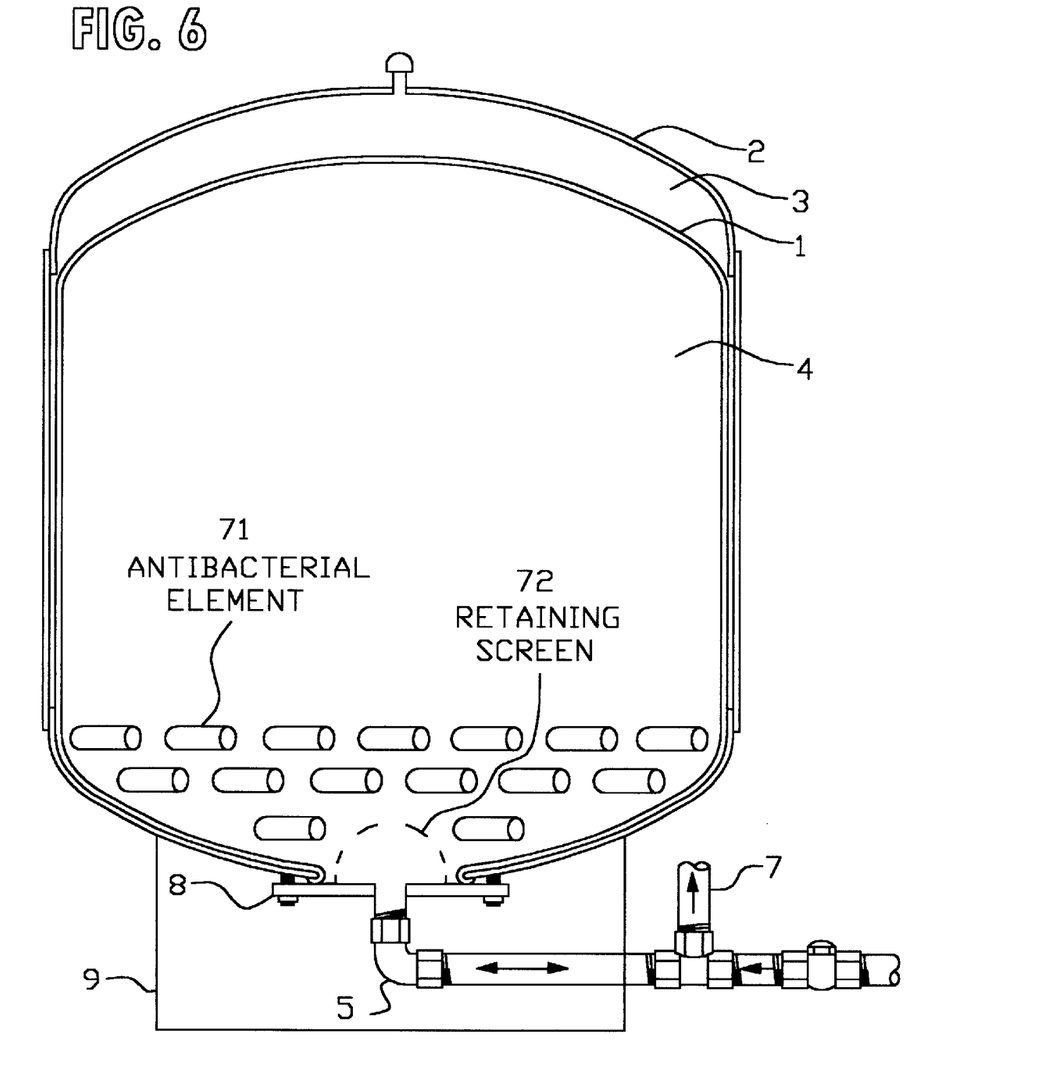
FIG. 6 shows a liquid storage and dispensing container according to a fifth embodiment of the invention, using an antibacterial element with a retaining screen.

In a fifth embodiment of the invention shown in FIG. 6, the sterilizer is an antibacterial element 71 placed within the liquid cavity 4 and secured by a retaining screen 72.

Figure 7:
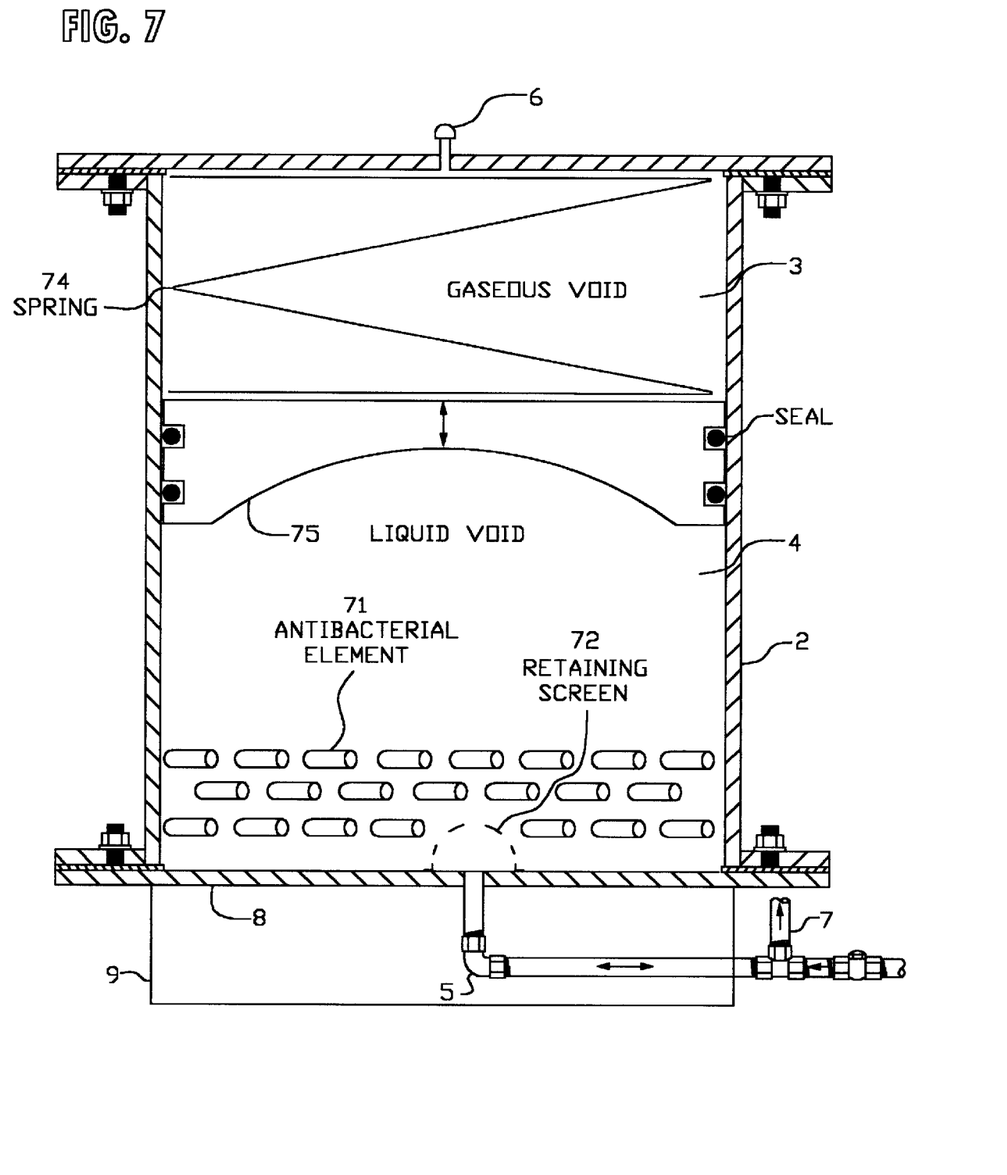
FIG. 7 shows a liquid storage and dispensing container according to an sixth embodiment of the invention, using an antibacterial element with a retaining screen.

According to a sixth embodiment of the invention shown in FIG. 7, the bladder 1 can be replaced with a rigid, movable member 75, having a seal 73. The rigid, movable member 75 may be held against the liquid 4 by a spring member 74 that is disposed in the gaseous void 3. In this embodiment of the invention, mechanical pressurizing means can be used in place of the pneumatic pressurizing means, and it is within the scope of the invention to use any of a variety of mechanical means to pressurize the liquid 4 other than that shown in FIG. 7.

Figure 8:
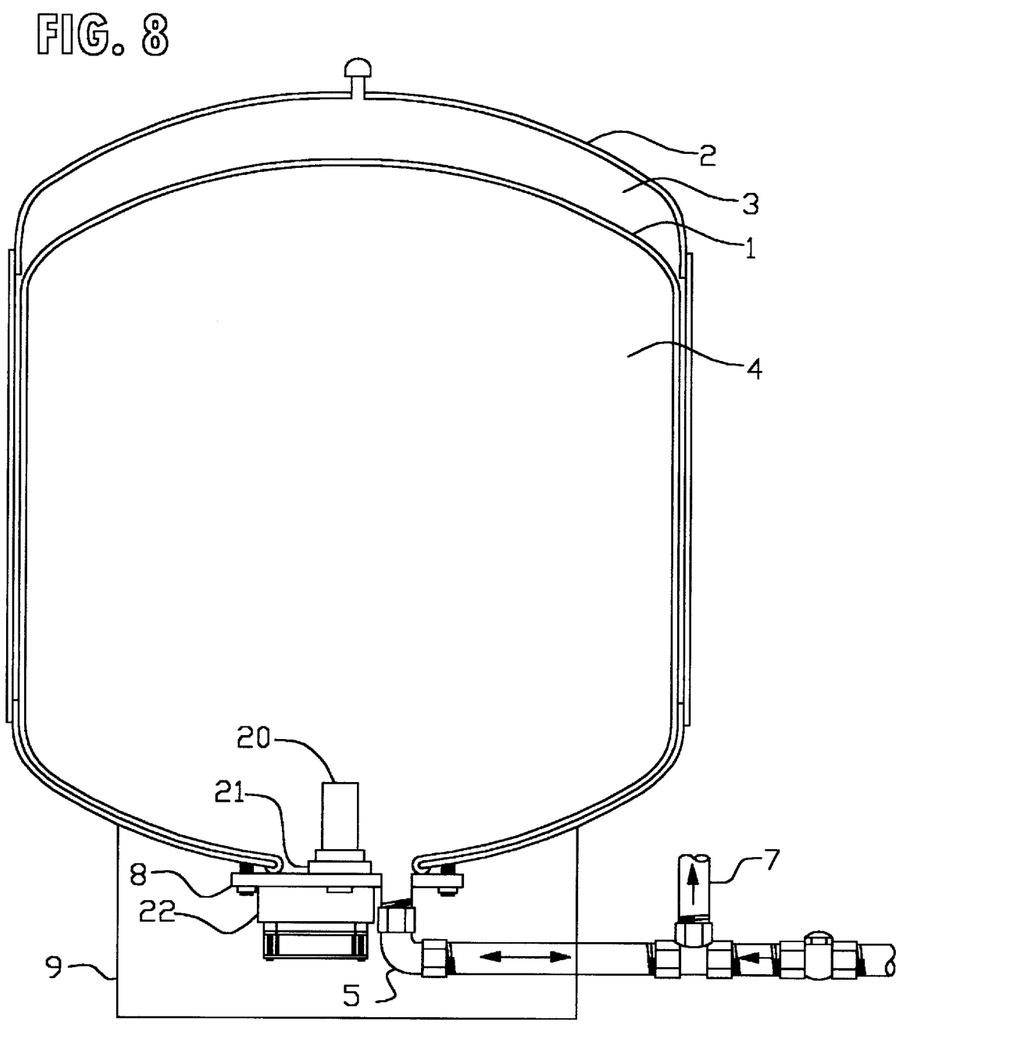
FIG. 8 shows a liquid storage and dispensing container according to a seventh embodiment of the invention, using a thermoelectric temperature adjustment unit.
Figure 9:
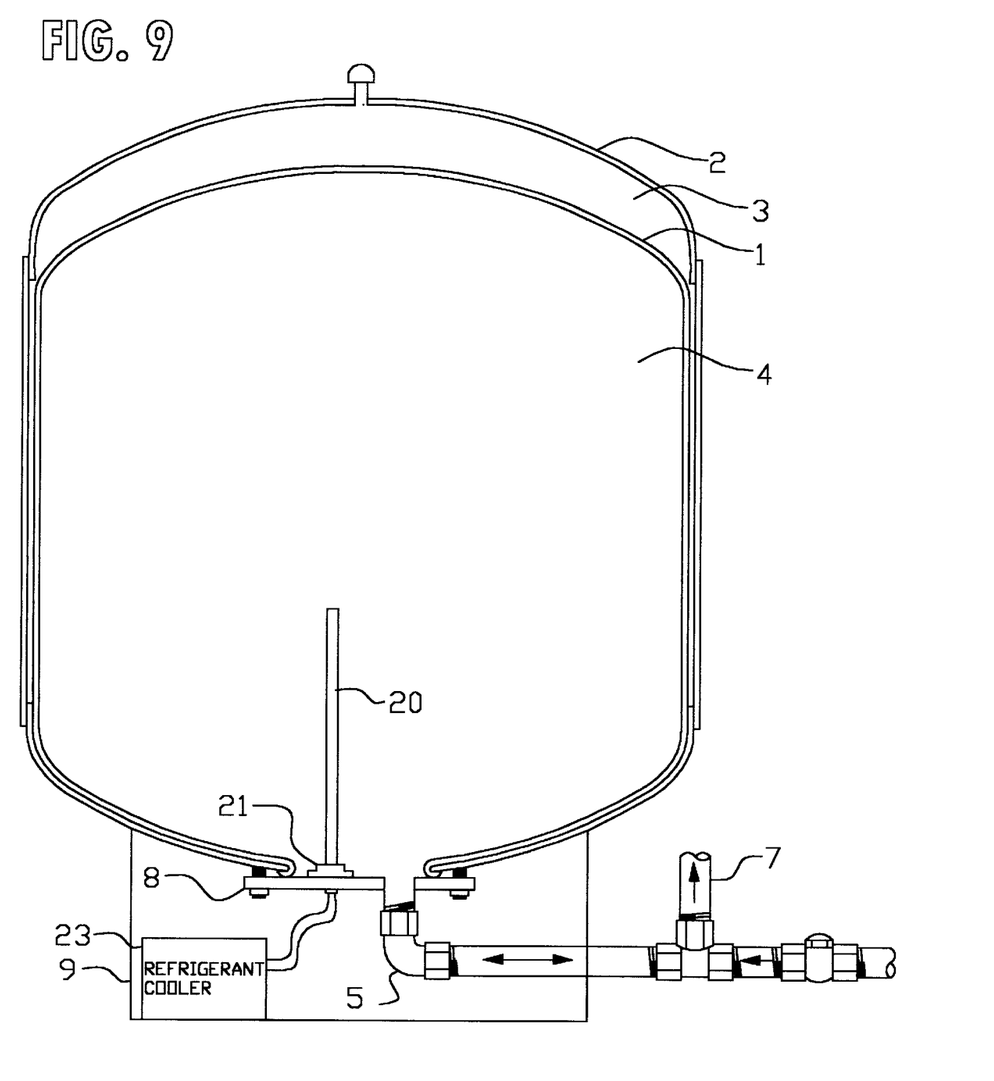
FIG. 9 shows a liquid storage and dispensing container, according to a eighth embodiment of the invention, using a conventional refrigerant temperature adjusting device.

According to a seventh embodiment of the invention, at least one cooling and heating component 20 may be disposed within the liquid 4, together with a sterilizing apparatus, or alone as shown in FIG. 8. The heating or cooling component 20 may be electrically powered, and automatically controlled using a power supply 24 which includes a transformer 51, wiring harness, temperature sensors 52, controls, etc. The cooling component can be a refrigerant cooler 23 as shown in FIG. 9, or a thermoelectric device 22 as shown in FIG. 8, or even a pettier cooler, which is a semiconductor-based electronic component that functions as a small heat pump. A cooling probe 20 is part of the thermoelectric device 22, and is inserted into the liquid 4 and conductively cools or heats the liquid 4. Insulation 56 may be utilized to cover the outer shell 2.

Figure 10:
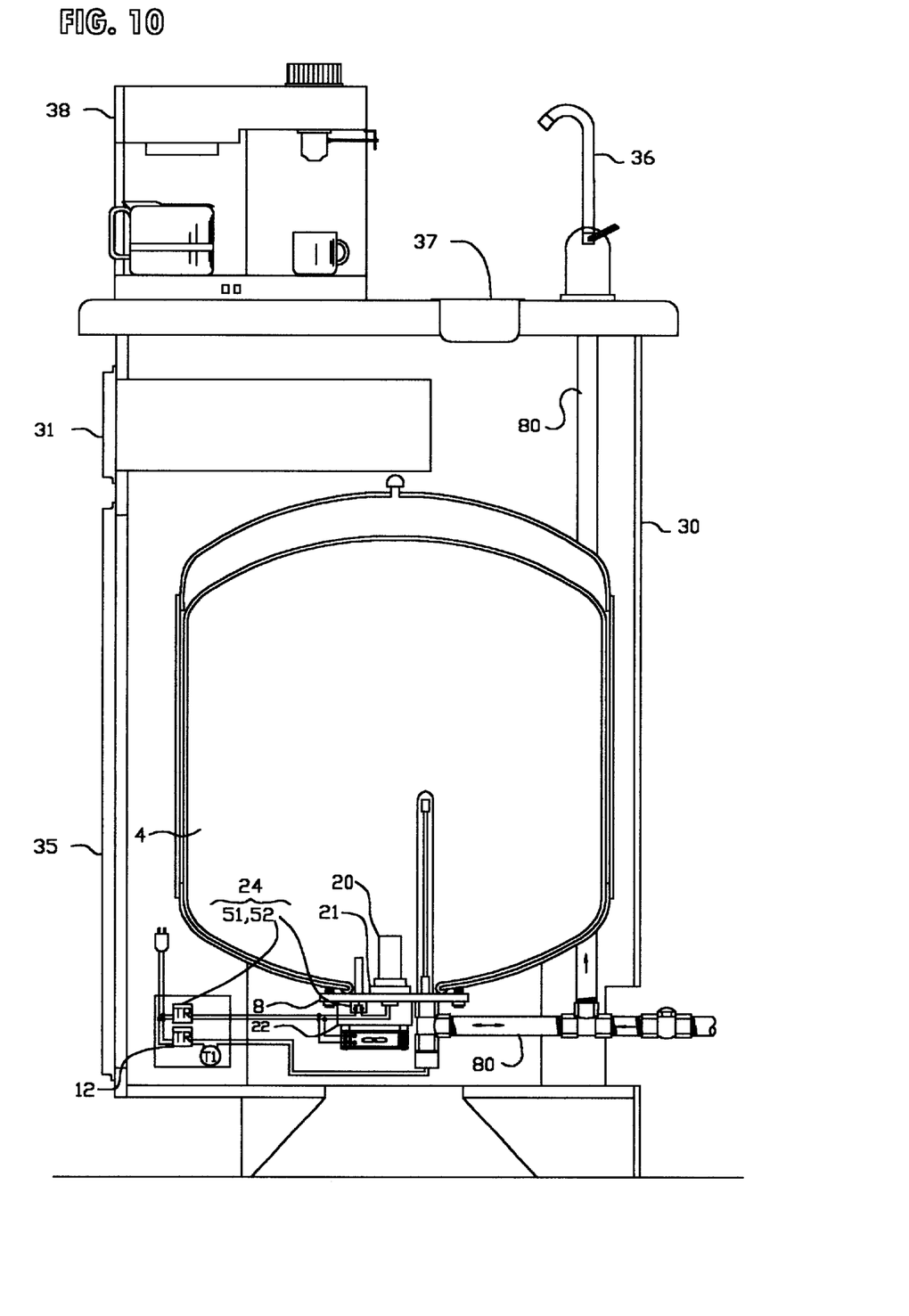
FIG. 10 shows a liquid storage and dispensing container according to the first embodiment of the invention, using a thermoelectric cooler, housed in a cabinet having drawers, a dispenser, an end user and a catch basin.

As just mentioned, a temperature sensor 52 may be included, and connected with the power supply 24 by a switching circuit as shown in FIG. 10. The thermoelectric device 22 may provide heat to the liquid 4 when the switching circuit connected to the thermoelectric device 22 is positioned in a first state, and the device 22 may also cool the liquid 4 when the switching circuit is positioned in a second state.

Figure 11:
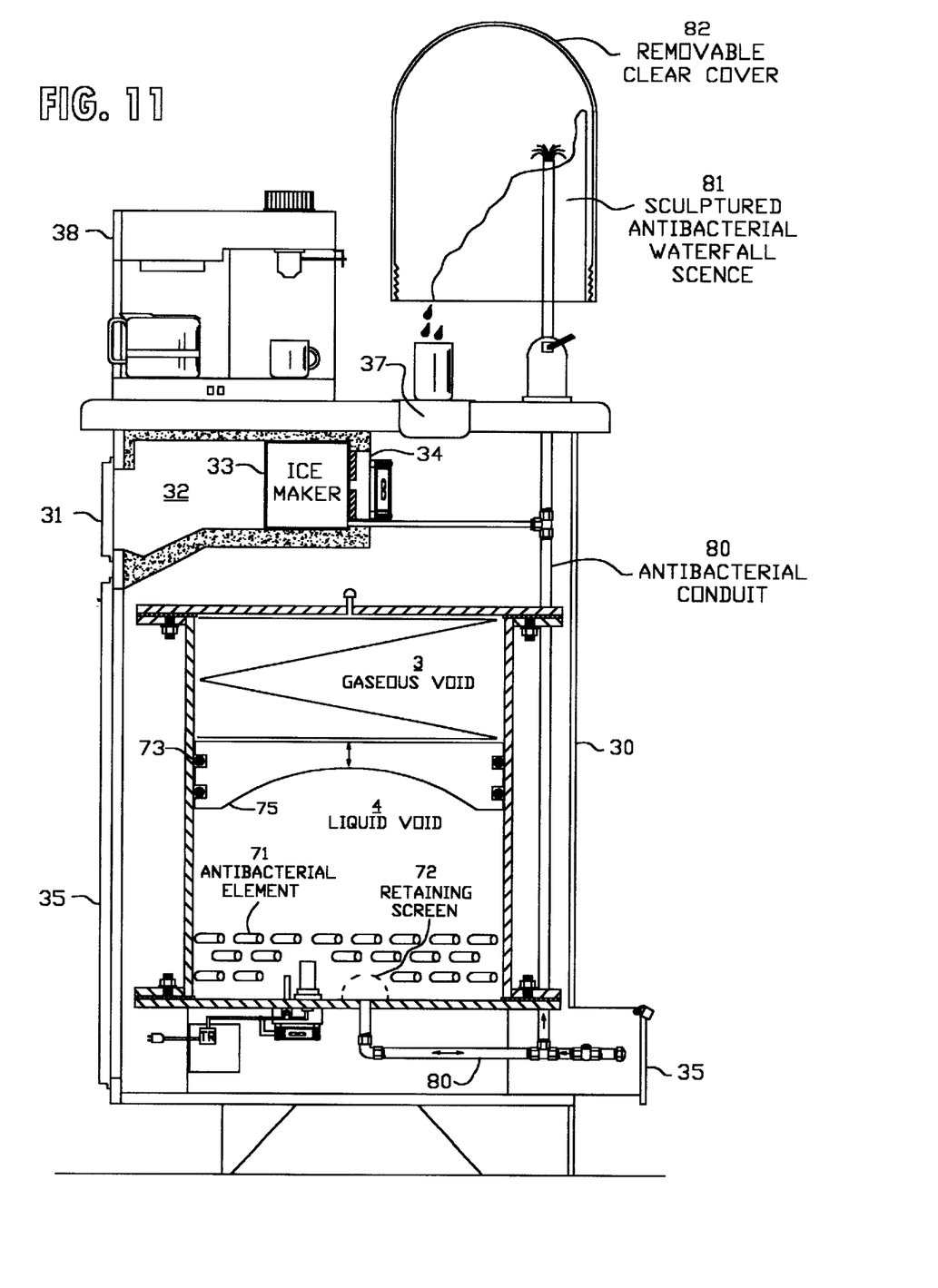
FIG. 11 shows a liquid storage and dispensing container according to a ninth embodiment of the invention, using a thermoelectric cooler, housed in a cabinet having an ice maker, an end user, a catch basin, a temperature control, an antibacterial conduit between the container and a graphic designed dispenser covered by a clear container such as glass.
Figure 12:
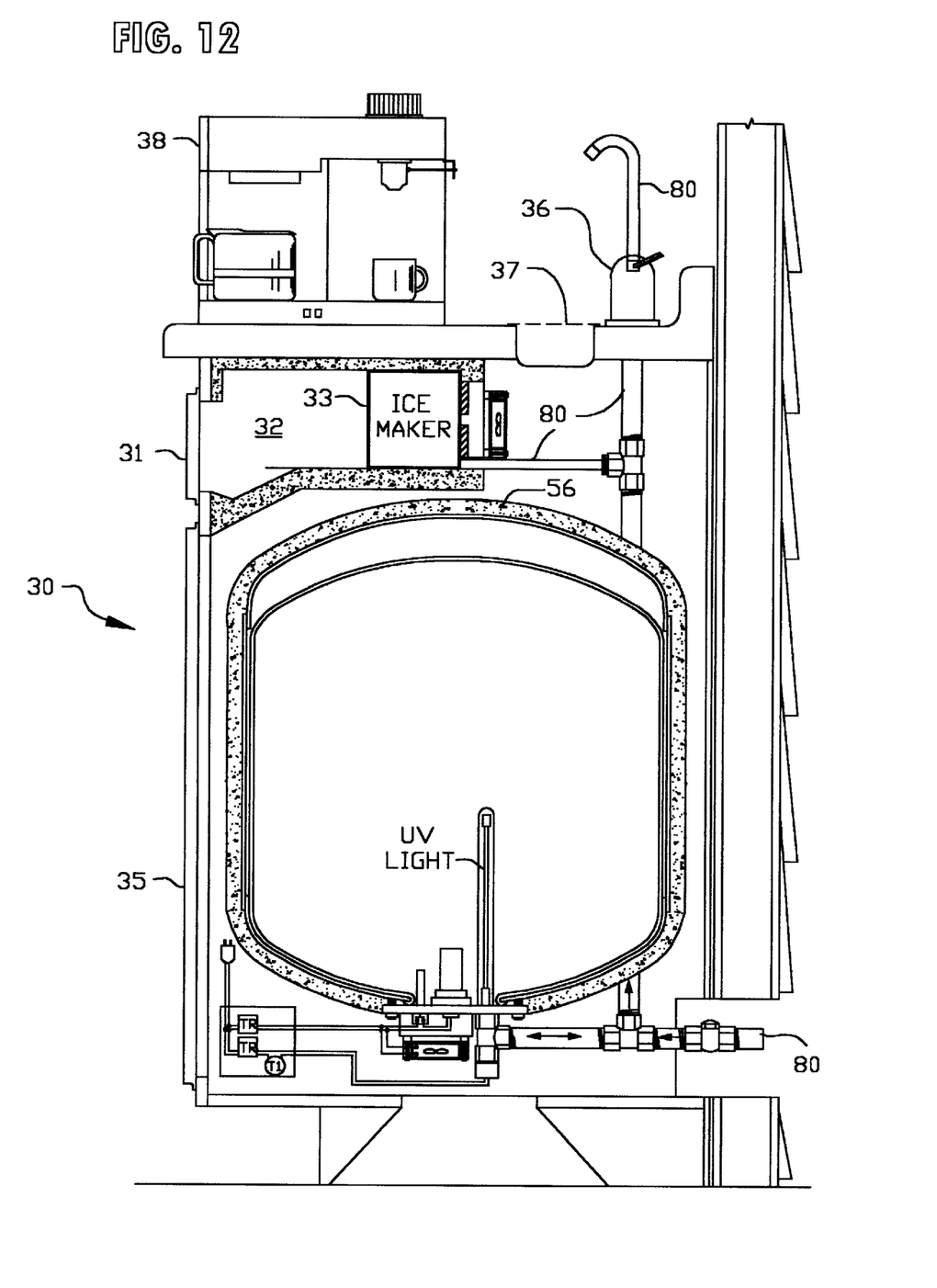
FIG. 12 shows a liquid storage and dispensing container according to the first embodiment of the invention, using a thermoelectric cooler and process control, housed in a cabinet with an access door, an ice maker, insulation and a bulk delivery access door.

In a preferred embodiment of the invention, the container with the sterilization system and heating and cooling system, along with the plumbing and electrical power supply and control are enclosed within a cabinet 30 as shown in FIGS. 10 to 12. A drawer 31 may be built into the cabinet 30 for storage space. An ice storage compartment 32 may be enclosed by the cabinet 30 as well as an ice maker 33, powered by a thermoelectric device 34 for example. Access to the container and other accessories may be provided by an access door 35 on the cabinet 30. A valved faucet 36 may also be provided. According to a ninth embodiment of the invention, an antibacterial conduit 80 is used to fill liquid void 4 and to dispense liquids from liquid void 4. Methods of producing an antibacterial conduit include silver impregnated conduit construction, conduit construction with ability to produce silver particles or conduit lined antibacterial elements, an antibacterial waterfall style to visibly display the liquid as it flows out dispenser 81 may be covered by a removable clear cover 82. A catch basin 37 may also be included to catch spilled liquid. Other facilities such as a source of drinking water use 38, i.e. a coffee maker, tea, cappuccino, soup, dehydrated foods, etc. may be included as an attachment to the cabinet 30.

Figure 15:
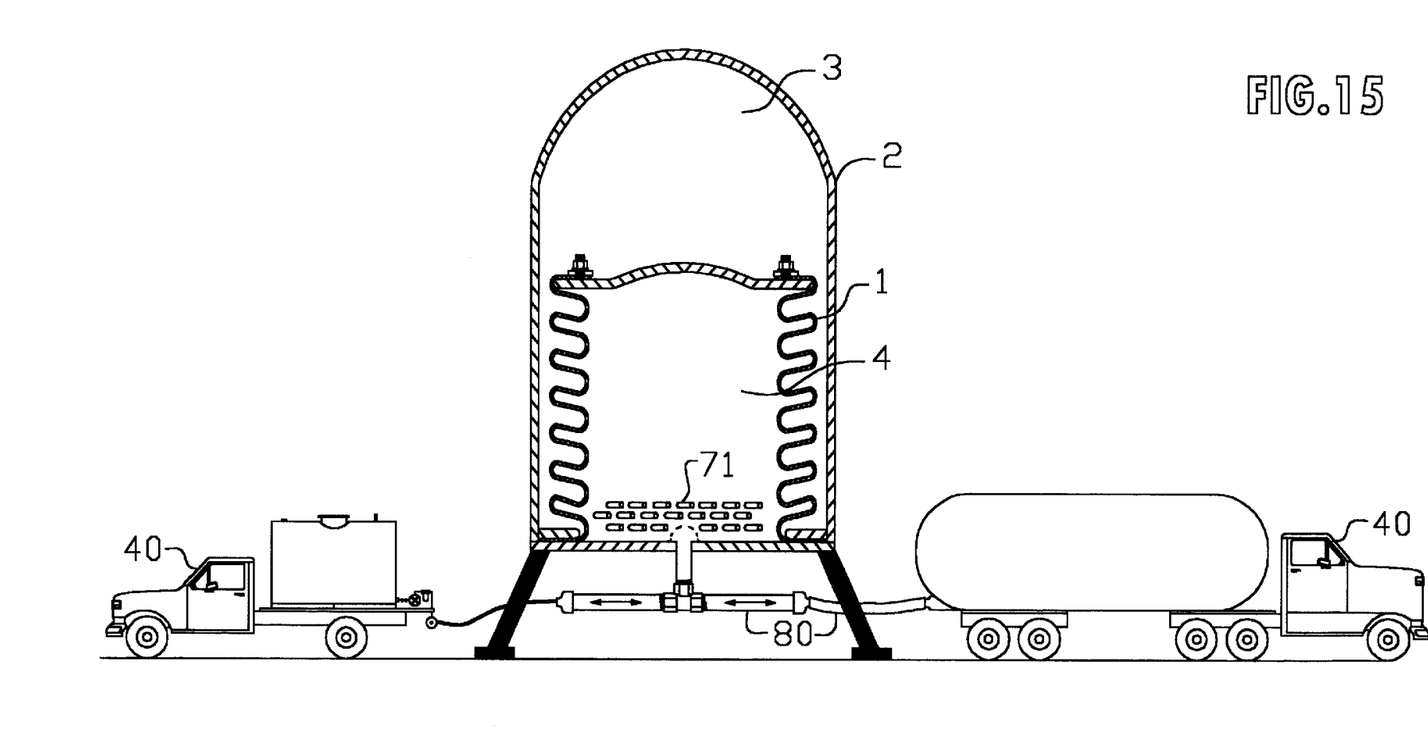
FIG. 15 shows a bulk size liquid storage and dispensing container according to a tenth embodiment of the invention, being serviced by various powered mobile bulk delivery units.

The apparatus of the present invention may be either stationary or mobile. The apparatus may vary in size from smaller end user sizes to central bulk storage sizes, as shown in FIG. 15 which displays a tenth embodiment of the invention. They may be serviced by other units that also may be assembled according to the invention as described above, or by atmospheric storage systems or plumbing conduit systems.

Figure 13:
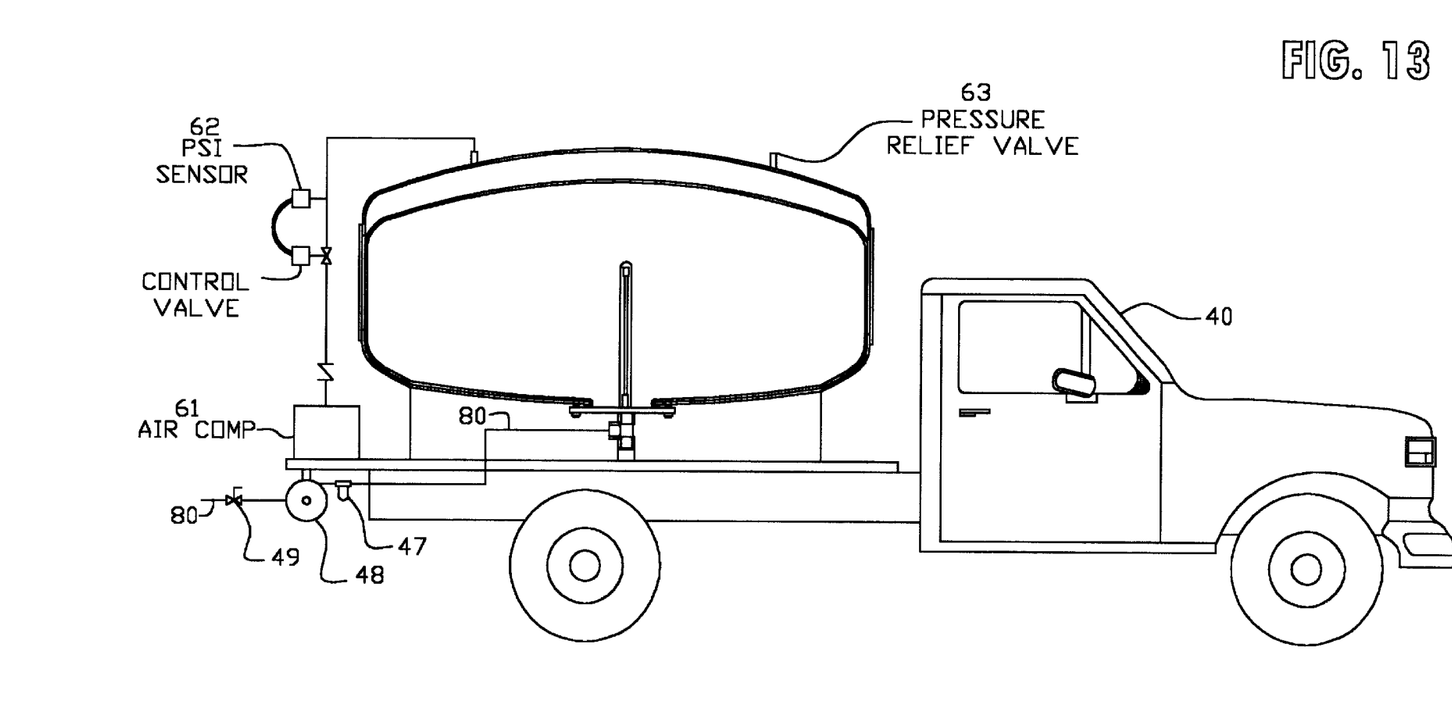
FIG. 13 shows a bulk delivery liquid storage and dispensing container according to the first embodiment of the invention, an air compressor, a pressure sensor and a pressure relief valve to maintain a given liquid pressure. The system is mounted on a delivery truck.

A powered mobile bulk delivery system such as a delivery truck 40 may be used in conjunction with the sterilizing/dispensing apparatus of the present invention. An antibacterial conduit 80 may be used to pump 46 the liquid 4 through a filter 47, a hose that may be connected to a reel 48, and a shut-off valve 49 into a storage/dispensing unit of the present invention, or from a storage/dipensing unit of the present invention that supplies the liquid 4 under pressure.

Figure 14:
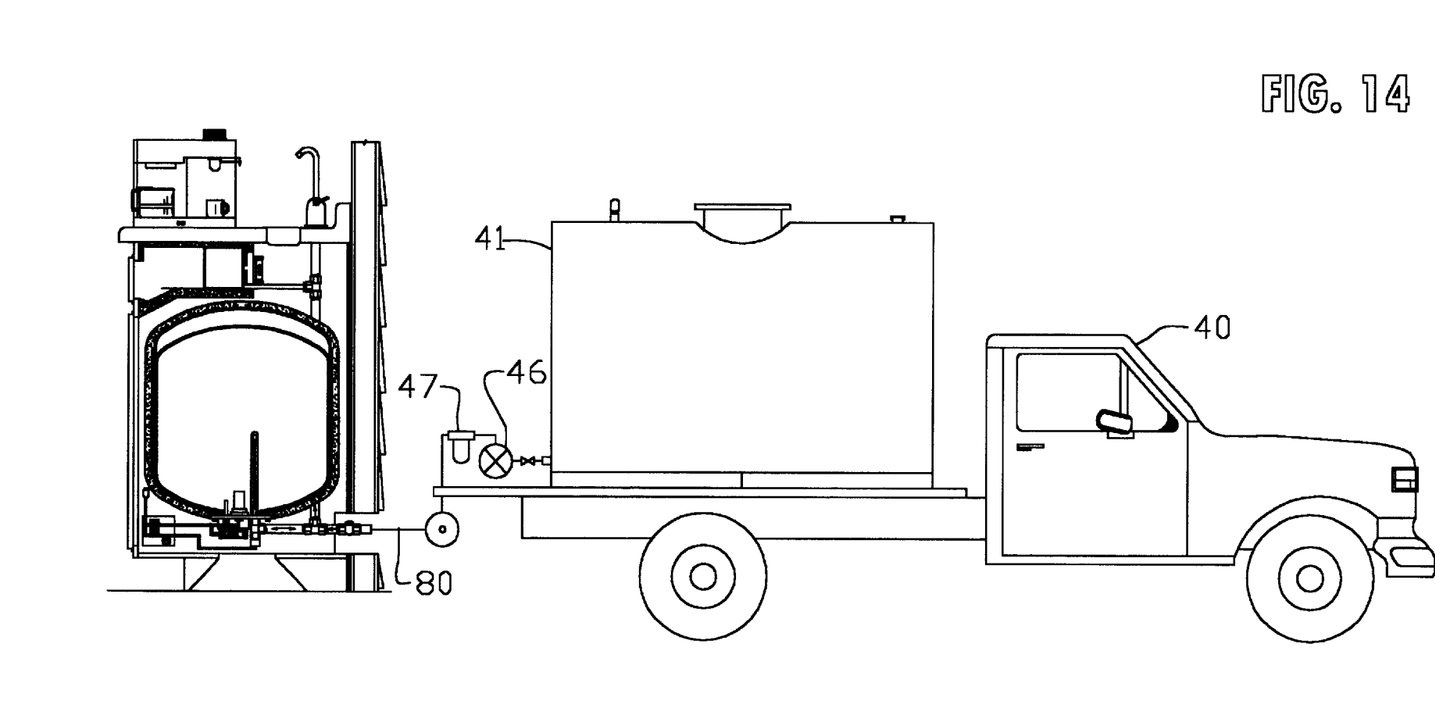
FIG. 14 shows a liquid storage and dispensing container according to the first embodiment of the invention, being filled by a bulk delivery truck with a conventional atmospheric tank.

As shown in FIG. 14, an atmospheric storage tank 41 may fill or be filled by a preferred embodiment of this invention.

It is recognized that while each of the figures show different types of sterilizing apparatuses with different types of liquid storage tanks, the various apparatuses are interchangeable, and can replace one another. Furthermore, although some of the sterilizing apparatuses are only shown in storage tanks that do not have a heating/cooling apparatus disposed therein, it is recognized that the heating/cooling apparatuses can be used alone or in conjunction with any of the sterilizing apparatuses shown, in any of the various storage tanks disclosed in the present application as well as with other types of storage tanks.

The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A method for containing and dispensing a liquid, which comprises the steps of:

providing a variable volume liquid container, said container having the capacity to be filled with and dispense a liquid while isolating said liquid from any gaseous substance, said variable volume liquid container having a sterilizer disposed within said liquid when said liquid is stored in said container, and dispensing said liquid from said container.

2. The method of claim 1 wherein said sterilizer is one or more devices selected from the group consisting of an ultraviolet light, an ultrasonic generator, a silver particle sterilizer, an antibacterial element, and an ozone generator and injection mechanism.

3. The method of claim 1 further comprising the steps of:

storing said liquid in said container; and pressurizing said liquid in said container by pressurizing a gas in a gas-containing portion of the container above atmospheric pressure.

4. The method of claim 3, further comprising the step of:

sterilizing said liquid while said liquid is stored in said container.

5. The method of claim 4, wherein said sterilizing step is performed automatically by using a timing device.

6. The method of claim 1, further comprising the step of:

adjusting a temperature of said liquid in said container to a predetermined temperature using a heating or cooling apparatus.

7. The method of claim 6, wherein said temperature adjusting step is performed automatically using a temperature sensor and adjuster.

8. The method of claim 6, wherein said temperature heating or cooling apparatus is selected from the group consisting of a thermoelectric heater, a thermoelectric cooler, a heat pump and a refrigerant cooler.

9. The method of claim 1,2,3,4,5,6,7, or 8 wherein in said dispensing step, said liquid is dispensed over a sculptured antibacterial water fall.

10. The method of claim 9, wherein in said dispensing step, said liquid is dispensed over a sculptured antibacterial water fall and said water fall is covered with a removable clear cover.

11. The method of claim 1 or 6, further comprising: filling said container with said liquid from a larger container that is part of a delivery system.

12. The method of claim 11, wherein said delivery system is a powered, mobile, bulk delivery system.

13. The method claim 1 or 6, further comprising: filling said container with said liquid from a smaller container that is part of a delivery system.

14. The method of claim 1 or 6, wherein said container is used as part of a powered, mobile, bulk delivery system.

15. The method of claim 1 further comprising providing a dispensing or filling conduit having sterilizing properties.

16. The method of claim 15, wherein said conduit sterilizing property is one of more devices selected from the group consisting of an antibacterial element impregnated conduit, an ultraviolet light and ultrasonic generator, a silver particle sterilizer, an antibacterial element and an ozone generator.

17. The method of claim 15 or 16, wherein said conduit sterilizing property is effective the substantial length of the conduit.

* * * * *